US008962306B2

(12) United States Patent
Cohen et al.

(10) Patent No.: US 8,962,306 B2
(45) Date of Patent: Feb. 24, 2015

(54) INSTRUMENTS AND METHOD RELATING TO THERMAL CYCLING

(75) Inventors: David Cohen, Dedham, MA (US); Sakari Viitamaki, Espoo (FI)

(73) Assignee: Thermo Fisher Scientific Oy, Vantan (FI)

( * ) Notice: Subject to any disclaimer, the term of this patent is extended or adjusted under 35 U.S.C. 154(b) by 1001 days.

(21) Appl. No.: 11/517,311

(22) Filed: Sep. 8, 2006

(65) Prior Publication Data

US 2008/0061429 A1 Mar. 13, 2008

(51) Int. Cl.
*C12M 1/34* (2006.01)
*B01L 7/00* (2006.01)

(52) U.S. Cl.
CPC .......... *B01L 7/52* (2013.01); *B01L 2300/0829* (2013.01); *B01L 2300/1822* (2013.01)
USPC .................. 435/287.2; 435/288.5; 435/303.1

(58) Field of Classification Search
CPC ............. B01L 7/52; B01L 2300/0829; B01L 2300/1822; B01L 3/50851; F25B 2500/09; F25B 2500/101
USPC .................. 435/287.2, 303.1, 809; 165/80.3; 62/3.3, 3.7; 136/204
See application file for complete search history.

(56) References Cited

U.S. PATENT DOCUMENTS 5,299,090 A * 3/1994 Brady et al. ................. 361/703
5,475,610 A 12/1995 Atwood et al.
6,295,202 B1 9/2001 Tucker et al.
6,308,771 B1 * 10/2001 Tavassoli ..................... 165/80.3
6,337,435 B1 * 1/2002 Chu et al. ...................... 136/242
6,372,486 B1 4/2002 Fripp et al.
6,429,007 B1 * 8/2002 Kluttz et al. .............. 435/286.5
6,657,169 B2 12/2003 Brown
2004/0241048 A1 12/2004 Shin et al.

FOREIGN PATENT DOCUMENTS

JP 3101844 A 4/1991
JP 5168459 A 7/1993
JP 11153367 A 6/1999
JP 2004103758 A 4/2004
JP 2004519650 A 7/2004
WO WO-02/070967 A1 9/2002

OTHER PUBLICATIONS

Japanese Office Action Issued in JP 2009-527167 on Jan. 31, 2012.
(Continued)

*Primary Examiner* — William H Beisner
(74) *Attorney, Agent, or Firm* — Wood, Herron & Evans, LLP

(57) ABSTRACT

The invention relates to a device for thermal cycling of biological samples, a heat sink used in such a device and a method. The heat sink comprises a base plate designed to fit in a good thermal contact against a generally planar thermoelectric element included in the device, and a plurality of heat transfer elements projecting away from the base plate. According to the invention the heat transfer elements of the heat sink and arranged in a non-parallel configuration with respect to each other for keeping the temperature of the base plate of the heat sink spatially uniform during thermal cycling.

19 Claims, 2 Drawing Sheets

(56) References Cited

OTHER PUBLICATIONS

Roche Applied Science, "LightCycler 480 Real-Time PCR System," System Brochure, 2005, pp. 1-6.

Roche Applied Science, "LightCycler 480 System, Rapid by Nature—Accurate by Design," Diagnostics System Brochure, pp. 1-16.

* cited by examiner

INSTRUMENTS AND METHOD RELATING TO THERMAL CYCLING

The present invention relates to devices for processing biological samples, especially but not exclusively for amplifying DNA sequences by the Polymerase Chain Reaction (abbreviated "PCR") method. In particular, the invention concerns a heat sink to be used in a thermal cycler which will be used for heating and cooling a plurality of biological samples. Such a heat sink typically comprises a base plate with an area from which waste heat is conducted into the heat sink, and a plurality of heat transfer elements which project away from the base plate and shed heat into a cooling medium such as air.

The invention also concerns a novel thermal cycler and a method of processing biological samples.

DESCRIPTION OF RELATED ART

Thermal cyclers are instruments commonly used in molecular biology for applications such as PCR and cycle sequencing, and a wide range of instruments are commercially available. A subset of these instruments, which include built-in capabilities for optical detection of the amplification of DNA, are referred to as "real-time" instruments. Although these can sometimes be used for different applications than non-real-time thermal cyclers, they operate under the same thermal and sample preparation parameters.

The core of a thermal cycler construct consists typically of: one or more thermoelectric modules (also: "thermoelements"), such as peltier elements, sandwiched in close thermal contact between the sample holder (also: "thermal block") and heat sink elements, along with one or more sensors in each of the sample holder and the heat sink, thermal interface materials on either side of the thermoelectric elements to enhance close thermal contact, and mechanical elements to fasten all of these components together.

The important parameters that govern how well a thermal cycler operates are: uniformity, accuracy and repeatability of thermal control for all the samples processed, ability to operate in the environment of choice, speed of operation, and sample throughput.

The uniformity, accuracy and repeatability of thermal control is critical, because the better the cycler is in these parameters, the more confidence can be placed in the results of the tests run. There is no threshold beyond which further improvement in these parameters is irrelevant. Further improvement is always beneficial.

The ability to operate in the environment of choice is less important for devices used in a laboratory setting where the samples are brought to it, but choices become limited when it is desired to use the instruments outside the laboratory and to bring it to where the samples are located. The two main concerns here involve the size and, thus, portability of the instrument, and the power requirements of the instrument. These two concerns are directly related, as the biggest single component in most cyclers is the heat sink used to reject the waste heat generated by the cycling. If a thermal cycler were to be built such that it only required enough power to operate off an automobile battery, it would also use a smaller heatsink because less waste heat was being generated. By further ensuring that the heat sink is engineered to be of high efficiency, the size can be minimized further and the instrument would become portable enough to operate virtually anywhere on earth.

Thermal cycling speed is important not just because it is a major factor in determining sample throughput, but also because the ability to amplify some products cleanly and precisely is enhanced or even enabled by faster thermal ramp rates. This can be particularly true during the annealing step that occurs on each cycle of an amplification protocol. During that time, primers are bonded onto the templates present, but if the temperature is not at the ideal temperature for this, not non-specific bonding can occur which in turn can lead to noise in the results of the reaction. By increasing ramp rate, the time that the reaction spends at non-ideal temperatures is reduced. It should be noted that an increase in ramp rate can be achieved by reducing the thermal capacitance of the samples and sample holders being cycled, or by increasing the thermal power supplied to the sample holder. These two methods can both be used in combination to increase speed over what is possible from either one alone. It should also be noted though that any increase in power supplied places additional load on the heat sink.

In thermal cyclers using conventional heat sinks, the temperature variation of the heat sink where it touches the thermoelements is caused by highly mismatched heat flux zones on the input and exhaust sides of the base plate. Restated simply, the thermoelements are located in a small central area of the heat sink base plate (the heat flux input zone), while the heat sink fins cover a much larger area of the opposing side of the heat sink base plate (the heat flux exhaust zone). This mismatch results in more rapid and efficient flow of heat from the edges of the input zone than the center, and thus a hot spot naturally occurs on the heat sink surface at the center of the thermoelements. Consequently, strong spatial variations in passive heat transfer through the thermoelements take place, which reflects to the temperature distribution of the samples to be thermally cycled. The problem of this kind of prior art is illustrated in FIG. 1.

Problems related to efficiency and thermal uniformity of the samples have previously been addressed in several publications.

U.S. Pat. No. 6,657,169 discloses a solution, which takes advantage of additional heating elements attached to the sample holder in order to improve the thermal uniformity of the holder. However, besides increasing the uniformity, the heaters also increase energy consumption of the device and increase complexity of the system.

US 2004/0,241,048 discloses a device which has an additional thermal diffusivity plate made of highly conductive material attached to the heat sink in order to convey heat to the heat sink more uniformly.

U.S. Pat. No. 5,475,610 discloses sample holder and microtiter plate designs which are meant to provide improved thermal uniformity. MJ Research Catalog 2000 also discloses one device structure, in which attention is paid on the thermal university of the samples during heating and cooling.

U.S. Pat. No. 6,372,486 discloses a thermal cycler having several sets of heating and cooling elements arranged in a array. By controlling each of the elements individually, the heating or cooling of the sample block can be adjusted. However, this solution significantly increases the costs and amount of control electronics of the device.

The LightCycler 480 System by Roche includes a heat pipe inserted in the heat sink. This solution increases the costs and complexity of the heat sink and thus the thermal cycling devices having such a heat sink.

Using any of the abovementioned methods of devices adds unwanted complexity to the final instrument in the form of added or parts which increase manufacturing costs and lower reliability. Using of additional active heating elements has the same disadvantages as noted above, but also power consumption is increased.

SUMMARY OF THE INVENTION

It is an aim of the present invention to provide a novel heat sink for use in a thermal cycler which will provide substantially improved thermal uniformity.

In particular, it in an aim of the invention to provide a heat sink that can improve the thermal uniformity of the samples in the sample holder during a thermal cycling process without adding additional components to the core of the thermal cycler instrument or without increasing the energy consumption of the device.

These and other objects, together with the advantages thereof over known methods and apparatuses, are achieved by the present invention, as hereinafter described and claimed.

The invention is based on the idea of increasing the thermal uniformity of the sample holder by increasing the thermal uniformity of the heat sink in the area where the thermoelement(s) (TE(s)) is/are in close thermal contact with the heat sink by shaping the heat dissipation volume of the heat sink, i.e., the volume defined by the heat transfer elements, appropriately. According to the invention, this is achieved by arranging the heat transfer elements connected to the base plate of the sink in a non-parallel (oblique) configuration. Consequently, the thermal uniformity of the base plate, and further the sample holder, is increased.

In its most common form, the heat sink according to the invention consists essentially of a base plate with an area from which waste heat is conducted into the heat sink, and heat transfer elements which project away from the base plate and shed heat into a cooling medium such as air. According to the invention, the heat transfer elements are mutually in a non-parallel configuration so as to provide weighed heat conveyance from the base plate to the ambient air. There may be other features also present, such as attachment points for other components or sealing flanges, but these are extraneous to the discussion at hand.

The thermal cycler according to the invention comprises a thermoelement sandwiched between a sample holder and a heat sink as described above so as to enable heating and cooling of the sample holder.

The method according to the invention comprises subjecting biological samples to a cyclic temperature regime, the samples being arranged in a sample-receiving plate, which is positioned on a sample holder of the thermal cycler. A heat sink is connected to the sample holder through a thermoelement so as to allow heating and cooling of the sample holder. In the method, heat is dissipated primarily through heat transfer elements of the heat sink which are arranged in non-parallel configuration with respect to each other.

According to an embodiment of the invention the heat transfer elements, which are typically in the form of metallic cooling fins, pin fins or thin folded heat exchangers, are arranged conically (in a broadening manner) such that the area where the heat transfer elements connect to the base plate of the heat sink is smaller than the cross-sectional heat dissipation area of the heat sink at a distance from the base plate. The broadening can take place in one dimension (typically two sides of the sink) or in two dimensions (all four sides of the sink).

Considerable advantages are obtained by means of the invention. First, by means of the invention the variations in passive thermal conductivity through the thermoelements is minimized. Passive thermal conductivity is always present when the sample holder and heat sink are at different temperatures, and the amount of heat conducted in this way is directly proportional to the difference in temperature between them. The passive heat flow can vary in quantity across the surface of the thermoelements to reflect the local variations in temperature on either side of them, thus resulting in a reflection of the non-uniform temperatures in the heat sink affecting the temperature uniformity of the sample holder. Reciprocally, if a more even temperature on the contact area of the thermoelements and the heat sink, as achieved my means of the present invention, also the temperature distribution of the sample holder remains more even.

In addition to improved uniformity, changing the fins from always being parallel to each other to being in a non-parallel configuration provides also advantages with respect to cycling efficiency and power consumption. Thus, it allows the area devoted to the base plate where the fins attach to be minimized, while allowing the area at the tips of the fins to be much wider, thus getting around constraints on how closely the fins can be spaced for manufacturing or airflow and back-pressure concerns. In other words, more usable heat rejection surface area (greater heat rejection volume) can be realized while minimizing or eliminating the heat flux mismatch described above.

For thermoelement-driven thermal cyclers according to FIG. 1 which are commercially for sale, dividing the fin attachment surface area of the base plate (including the surface of the spaces between fins) by the area covered by the thermoelements (including the space if any between any individual thermoelement modules) results in a factor of at least 2 and often more. This leads to a great spatial temperature mismatch in the sample holder. Reducing this factor would result in improved thermal uniformity of the heat sink and thus the sample holder, but doing so with a conventional heat sink would reduce the heat rejection surface area so much that the system would overheat or the system would be forced to reduce the power load and thus reduce the speed of the system. By means of a heat sink according to the present invention the amount of mismatch may be reduced without having to compromise the speed significantly or at all.

In the prior art, increasing the thermal uniformity of the heat sink where it is in contact with the thermoelement is done by actively correcting for am, non-uniformities that are present. As described in more detail above, this can be done by using targeted zone heaters or heat spreading mechanisms (solid high conductivity spreader plates, liquid-vapor heat pipes, or similar devices), but these solutions add components and complexity. In contrast to these prior art methods (which can be characterized as being "brute force"-methods), the present invention addresses the root problem of why non-uniform temperatures happen in the first place, that is, the phenomenon behind the non-uniformity.

Sample throughput needs vary from assay to assay and from user to user. The invention described here is however independent of sample throughput considerations, and is applicable across a wide range of capacities.

By the term "base plate" of the heat sink we mean any member that serves as a fixing point of the heat transfer elements contained in the heat sink and provides a suitable heat transfer surface which can be thermally well coupled to the thermoelement.

Although this document generally describes the direction of the flow of heat to be from the thermoelement to the ambient air through the heat transfer elements of the heat sink (cooling cycle), a person skilled in the art understands that the flow may be reversed as well (eating cycle).

Next, the invention will be described more closely with reference to the attached drawings, which represent only exemplary embodiments of the invention.

DETAILED DESCRIPTION OF THE INVENTION

Figure 2:
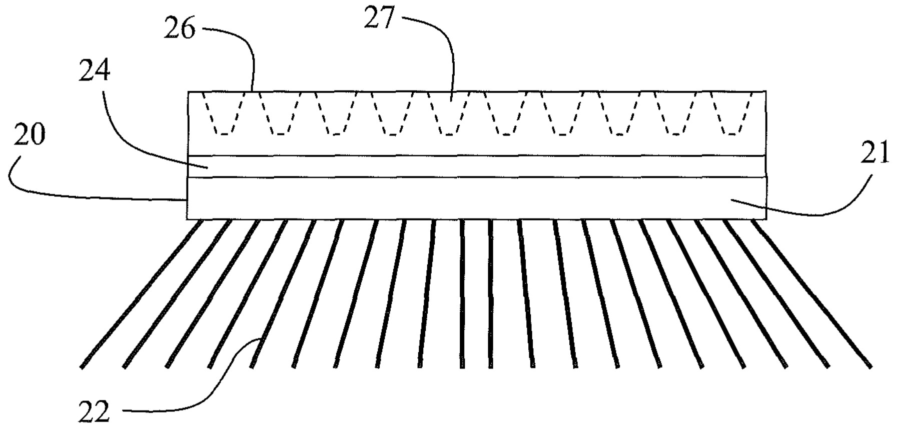
FIG. 2 depicts a cross-sectional view of a core of a thermal cycler according to one embodiment of the present invention.
Figure 3:
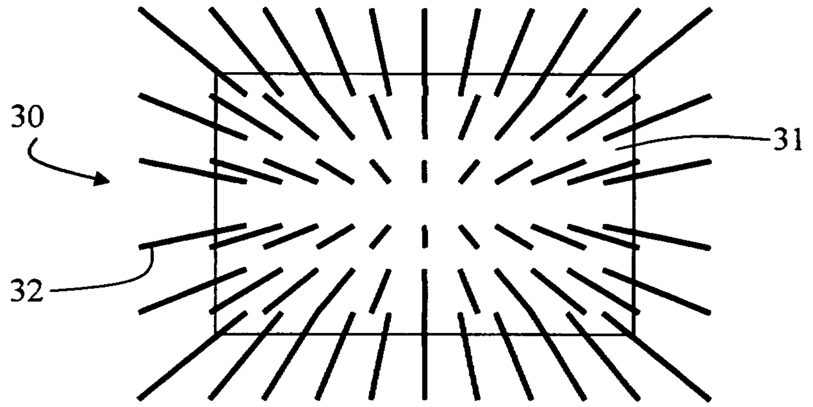
FIG. 3 shows a bottom view of a heat sink according to one embodiment of the present invention.
Figure 4:
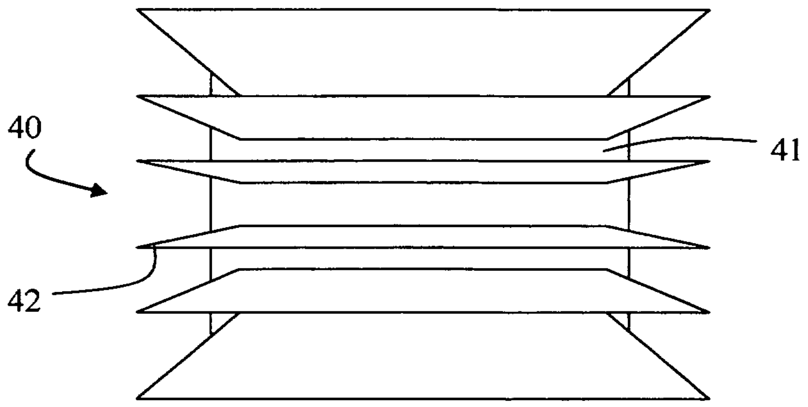
FIG. 4 shows a bottom view of a heat sink according to another embodiment of the present invention.

The general principle of the invention is shown in FIG. 2. A sample holder 26, a peltier element 24 and heat sink 20 are stacked so as to form a core of a thermal cycler instrument. Between the parts, there is typically thermally well conducting agent applied. The heat sink comprises a base plate 21 and a plurality of heat transfer elements 22. In the embodiment shown in the figure, the heat transfer elements 22 are aligned uniformly pitched and having growing angle with respect to the normal axis of the base plate towards the lateral portions of the plate. It should be noted that non-parallel nature of the heat transfer elements in one dimension only is shown in the Figure. If fins or fin pins are used as heat transfer elements, there may or may not be a corresponding alignment also in a direction perpendicular to the image plane. A two-dimensional fin configuration is shown in FIG. 3. In the case of plates, the edges of the plates may be non-parallel, as shown in FIG. 4.

Common to the embodiments described above is that the heat transfer elements are oriented in a fan-like manner such that the footprint of the elements at a distance from the base plate is larger than the footprint of the elements near the area of contact of the elements and the base plate. More generally, it can also be said that the heat transfer elements of the heat sink are preferably oriented in a non-parallel configuration such that the heat dissipation capacity of the heat sink is spatially essentially evenly distributed across the base plate so as to minimize variations in passive heat transfer through the thermoelectric element during heating and cooling of the sample holder. Non-parallelity of the protruding portions of the heat sink compensates for the limited size of the base plate (and the peltier module) and causes the temperature of the upper side of the base plate to remain at even temperature. Thus, no "hot spot" is formed in the middle portion of the base plate, such as in some prior art solutions.

The spacing between the neighboring heat transfer elements is thus typically increasing when moved away from the base plate, i.e., there is a considareble angle between neighboring elements. The angle can also be non-constant in along the length of the elements. Also when viewed in the plane of the base plate, the angle may vary between different element pairs. In addition or alternatively the heat transfer elements may be initially non-uniformly pitched to the base plate. Both described methods have an effect on the spatial heat dissipation capacity of the sink.

The heat transfer elements can have the form of fins, fin pins, straight plates, pleated plates, or any other solid member in the form of an extended surface experiencing energy transfer by conduction within its boundaries, as well as energy transfer with its surroundings by convection and/or radiation, used to enhance heat transfer by increasing surface area.

The heat sink can be made of many different materials including aluminum, copper, silver, magnesium, silicon carbide and others, either singly or in combination. It also can be fabricated by any common method of manufacturing heat sinks, including extrusion, casting, machining, or fabrication techniques, either in entirety or in combination with simple finishing via machining. Most advantageously, the heat sink consists of a single continuous (unitary) piece. The even heat distribution is achieved solely by the proper alignment of the heat transfer elements, whereby there is typically no need for separate heat diffusion blocks, heat conductor arrangements or additional active heaters or coolers.

The thermoelement used in connection with the present heat sink is preferably a peltier unit comprising one or more individual peltier modules. Multiple peltier modules may be driven in parallel without individual temperature control.

The sample holder may be of any known type. Typically it is fabricated from aluminium or comparable metal and is shaped to accommodate microtiter plates according to SBS standards (Society for Biomolecular Screening). Thus, on the top surface of the holder, there are a plurality of wells arranged in a grid. The bottoms of the wells are formed to tightly fit against the outer walls of the microtiter plates so as to provide good thermal connection between the holder and the plate. In a preferred embodiment, a sample holder designed for v-bottomed (or u-bottomed) plates is used.

Figure 1:
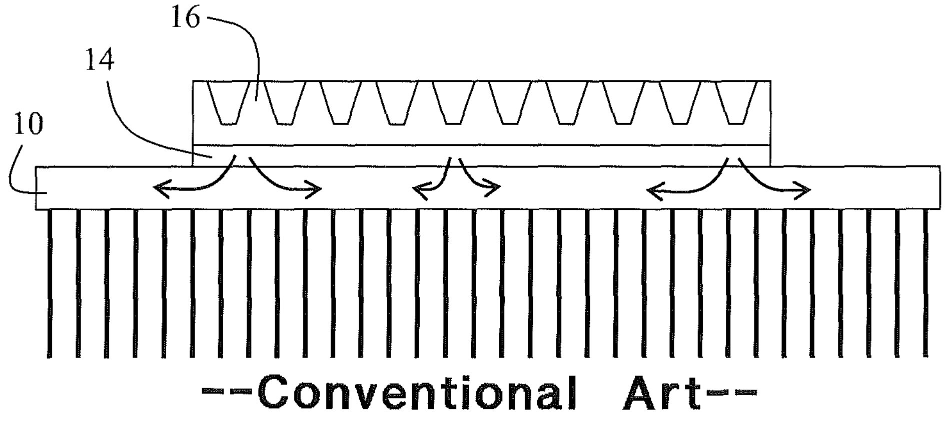
FIG. 1 shows a cross-sectional view of a typical core of a thermal cycler according to prior art.

Preferably, the footprints of the thermoelement and the base plate of the heat sink are essentially equal. Thus, no increased heat flow takes place at the lateral portions of the heat sink (cf. FIG. 1). Typically also the footprint of the sample holder corresponds to the areas of the heat sink and the thermoelement. Typically, the abovementioned footprints correspond roughly to the footprint of SBS standard mictotiter plates, but the heat sink according to the invention may also be manufactured to any other size or shape, depending among other things on the microtiter plate format used. Also the exact heat transfer element configuration of the heat sink has an effect on the preferred size of the base plate.

According to a preferred embodiment of the invention, a fan directed to the heat rejection zone (i.e., between the heat transfer elements) of the heat sink is used during cycling. This significantly increases the energy transfer rate from the heat sink to the ambient air.

According to a further embodiment, the device according to the invention is a lightweight portable thermal cycler, possibly operated by a battery. Such a device can be used in field circumstances, i.e., where the biological samples to be analyzed are in the fast place. In field circumstances, the benefits provided by the heat sink at hand, i.e., compact and simple form and low energy consumption, are emphasized.

The invention may also be used in connection with other solutions for increasing thermal uniformity or efficiency of thermal cyclers, for example those referred to as prior art in this document. However, it has been found that shaping of the heat sink according to the invention is usually sufficient for practically eliminating the temperature non-uniformity caused by conventional heat sinks and thermal cyclers.

Many different configurations are possible within the scope of this invention, including variations on part geometries, methods of assemblies and configurations of parts relative to each other. The description here is meant to illustrate and represent some possible embodiments of the invention.

The invention in not limited to the embodiments presented above in the description and drawings, but it may vary within the full scope of the following claims. The embodiments defined in the dependent claims, and in the description above, may be freely combined.

The invention claimed is:

1. A thermal cycling instrument for processing biological samples, comprising a sample holder designed to receive a plurality of biological samples, a heat sink comprising a base plate and a plurality of heat transfer elements projecting away from the base plate, a thermoelectric element sandwiched between the sample holder and the base plate of the heat sink, wherein the heat transfer elements of the heat sink are arranged in a non-parallel fan-like configuration with respect to each other, such that the footprint of the elements at a distance from the base plate is larger than the footprint of the elements near the area of contact of the elements for keeping the temperature of the base plate of the heat sink spatially uniform, and the base plate has a footprint substantially equal to the footprint of the sample holder.

2. The instrument according to claim 1, wherein the thermoelectric element comprises at least one peltier element thermally connected to the sample holder and the heat sink.

3. The instrument according to claim 1, wherein the heat transfer elements of the heat sink are oriented such that the heat dissipation capacity of the heat sink is spatially essentially evenly distributed across the base plate so as to minimize variations in passive heat transfer through the thermoelectric element during heating and cooling of the sample holder.

4. The instrument according to claim 3, wherein the majority of the heat transfer elements are oblique with respect to the normal of the base plate, the angle of the lateral elements being regularly larger than the angle of the inner elements.

5. The instrument according to claim 1, wherein the heat transfer elements have the form of fins or fin pins.

6. The instrument according to claim 1, wherein the heat transfer elements are planar or pleated.

7. The instrument according to claim 1, wherein the heat sink is formed of a unitary piece of metal.

8. The instrument according to claim 1, which comprises a fan for forcedly circulating air between the heat transfer elements of the heat sink.

9. The instrument according to claim 1, which is portable and adapted to be operated by batteries.

10. An instrument according to claim 1, further comprising a fan for forcedly circulating air between the heat transfer elements of the heat sink.

11. A thermal cycling instrument for processing biological samples according to claim 1, wherein the heat transfer elements comprise fin pins.

12. A method for processing biological samples, comprising subjecting a plurality of biological samples to a temperature cycling regime in a thermal cycling instrument, which comprises the steps of:

providing a sample holder designed to receive a plurality of biological samples, providing a heat sink comprising a base plate and a plurality of heat transfer elements projecting away from the base plate, and providing a thermoelectric element sandwiched between the sample holder and the base plate of the heat sink, keeping the temperature of the base plate of the heat sink spatially uniform by arranging the heat transfer elements in a fan-like and non-parallel configuration with respect to each other, such that the footprint of the elements at a distance from the base plate is larger than the footprint of the elements near the area of contact of the elements and the base plate, and using a base plate and a sample holder which have substantially equal footprints.

13. The method according to claim 12, wherein at least one peltier element thermally connected to the sample holder and the heat sink is used as the thermoelectric element.

14. The method according to claim 12, wherein a heat sink is used, where the heat transfer elements are oriented such that the heat dissipation capacity of the heat sink is spatially essentially evenly distributed across the base plate so as to minimize variations in passive heat transfer through the thermoelectric element during heating and cooling of the sample holder.

15. The method according to claim 14, wherein a heat sink is used, where the majority of the heat transfer elements are oblique with respect to the normal of the base plate, the angle of the lateral elements being regularly larger than the angle of the inner elements.

16. The method according to claim 12, wherein a heat sink having heat transfer elements in the form of fins or fin pins is used.

17. The method according to claim 12, wherein a heat sink having planar or pleated heat transfer elements is used.

18. The method according to claim 12, wherein a heat sink formed of a unitary piece of metal is used.

19. The method according to claim 12, which comprises forcedly circulating air between the heat transfer elements of the heat sink.

* * * * *